United States Patent
Reisfeld et al.

(10) Patent No.: US 6,562,424 B1
(45) Date of Patent: May 13, 2003

(54) PHOTOCHEMICAL SENSORS AND METHOD FOR THE PRODUCTION THEREOF

(75) Inventors: Renata Reisfeld, Jerusalem (IL); Dimitri Shamrakov, Jerusalem (IL)

(73) Assignee: Yissum Research Development Company, Jerusalem (IL)

( * ) Notice: Subject to any disclaimer, the term of this patent is extended or adjusted under 35 U.S.C. 154(b) by 0 days.

(21) Appl. No.: 09/496,641

(22) Filed: Feb. 3, 2000

Related U.S. Application Data

(63) Continuation-in-part of application No. 09/012,005, filed on Jan. 22, 1998, now abandoned.

(51) Int. Cl.⁷ .................. B28B 21/00; B28B 21/72; B28B 23/08; B29D 22/00; B29D 23/00
(52) U.S. Cl. .............. 428/34.7; 428/690; 428/34.1; 428/34.4; 372/53
(58) Field of Search ................ 428/690, 34.1, 428/34.4, 34.7, 34.6; 372/53, 20, 40; 264/1.24

(56) References Cited

U.S. PATENT DOCUMENTS 5,222,092 A * 6/1993 Hench et al. ............... 372/53
5,783,319 A * 7/1998 Reisfeld et al. ............ 428/690

FOREIGN PATENT DOCUMENTS

WO       95/15021    * 6/1995 ............. H01S/3/06

OTHER PUBLICATIONS

"Optical Fluorescence Sensors for Continuous measurement of Chemical Concentrations in Biological Systems" by Lubbers et al, Sensors and Actuators, 4 (1983) 641–654.
Complex Formation and Fluorescence Part 1, Anal. Chem. ACTA, 29 (1963) 172–177.
"A Fluorescent Sensor for Aluminum(III), Magnesium(II), Zinc(II) and Cadmium(II) Based on Electrostatically Immobilized Quinolin–8–OL Sulfonate" by Zhang Zhujun et al, 1985 Elsevier Science Publishers, Amsterdam, 1985.
Applied Spectroscopy, vol. 45, No. 9, 1991, pp. 1509–1515.
"Chemical Sensors Based on Fiber Optics" by W. Seitz, Analytical Chemistry, vol. 56, No. 1, Jan. 1984.
"Chemical Sensors" by Jiri Janata et al, 1988 American Chemical Society, vol. 60, No. 12, Jun. 15, 1988.
"A Field–Deployable Dual–Wavelength Fiber–Optic pH Sensor Instrument Based on Solid–State Optical and Electrical Components" Jones et al, Applied Spectroscopy, vol. 45, No. 8, 1991.
"Membrane for IN SITU Optical Detection of Organic Nitro Compounds Based on Fluorescence Quenching" by Jian et al, Elsevier Science Publishers, 1990.
Luminescence Spectroscopy, Analytical Chemistry (1972), Wiley–Interscience, pp. 271–279.
"Fiber–Optic Organic Vapor Sensor" Barnard et al, Environ. Sci. Technol. 1991, vol. 25, No. 7, 1301–1304.
Doped Sol–Gel Glasses as pH Sensors by Rottman et al, Elsevier Science Publishers, Materials Letters 13 (1992), 293–298.
"Photochemical Sensor Based on Malachite Green in Glass Films" by Chernyak et al, Sensors and Materials, 4 4 (1993) 195–04.
"Optical properties of Colorants of Luminescent Species in Sol–Gel Glasses", by Reisfeld et al, Structure and Bonding, 1992.

(List continued on next page.)

Primary Examiner—Harold Pyon
Assistant Examiner—Michael C. Miggins
(74) Attorney, Agent, or Firm—Sughrue Mion, PLLC

(57) ABSTRACT

The invention provides an indicator dye nanoporous photochemical sensor composite glass film, comprising a multiplicity of polyacrylate chains intertwined with a multiplicity of cross-linked networks of silica and doped with an indicator dye, wherein the film is formed with a plurality of nanopores sized in the range between 20 and 200 angstrom for the entry of analytes to be detected thereby.

10 Claims, 6 Drawing Sheets

Change in the absorption spectrum of malachite green in sol - gel film when exposed to the gaseous ammonia. 1 → 2.

OTHER PUBLICATIONS

"Oxazine–170 in Sol–Gel Glass and PMMA Films as a Reversible Optical Waveguide Sensor for Ammonia and Acids" by Chernyak et al, Sensors and Materials, 2,2 (1990) pp. 117–126.

"Synthesis of p–Azobenzenediazoaminoazobenzene Sulfuric Acid and its Application for Spectrophotometric Determination of Cadmium" by Yurui, Analytical Letters 25(2), 1992 331–338.

* cited by examiner

The absorption (left) and emission (right) spectra of neutral 1,3 and cationic 2,4 forms of Oxazine - 170 in the sol - gel film.

The neutral (left) and cationic (right) forms of Oxazine - 170.

The neutral, monocation and dication forms of the malachite green dye downward.

Change in the absorption spectrum of malachite green in sol - gel film when exposured to the gaseous ammonia. 1 → 2.

pH sensitivity of sol - gel film sensor doped with malachite green as immersed entirely in the solutions with different pH.

Optrode configuration for ammonium ions measurement. 1 - sensing body, 2 - polymer membrane, 3 - liquid membrane with NaOH, 4 - optical fiber.

Response of the sensor with the Rhodamine 6G dye on the chloroform vapor presence. 1 - blank, 2 - altered.

Response of the sensor with the Oxazine 170 dye on the dichloroethane vapor presence. 1 - blank, 2 - altered.

The Measurement Scheme.

PHOTOCHEMICAL SENSORS AND METHOD FOR THE PRODUCTION THEREOF

The present specification is a continuation-in-part of U.S. Ser. No. 09/012,005, filed Jan. 22, 1998, now abandoned, the relevant teachings of which are incorporated herein by reference in their entirety for all purposes.

The present invention relates to photochemical sensors and methods for the production thereof.

BACKGROUND OF INVENTION

More particularly, the present invention relates to an indicator dye nanoporous photochemical sensor composite glass films and processes for the preparation thereof, as well as to the use thereof in the preparation of a fiber optic and/or wave-guiding photochemical sensor for detecting environmental impurities.

The present invention enables the preparation of stable, multi-use remote sensors for detection systems for environmental impurities which allow monitoring in situ of traces of impurities such as ammonia, acid rain and bases in the atmosphere, the water and the ground, and chlorinated hydrocarbons in ground waters and soils, based on the introduction of indicator dyes into a novel composite glass film from which sensitive waveguides are fabricated.

The concept of applying optical guides and fiber optical sensors to the detection of various environmental impurities is not new, and has been pursued for over a decade. (See, e.g., W. R. Seitz, "Chemical Sensors Based on fiber Optics," *Anal. Chem.*, Vol. 56, p. 16A (1984); D. W. Luebbers and N. Opitz, "Optical Fluorescence Sensors for Continuous Measurements of Chemical Concentration in Biological Systems," *Sensors Actuators*, Vol. 4, p. 641 (1983); and E. J. Poziomek, "Fiber Optic Sensors, A Review," *Proc. of the Third Biennial Dept. of Defense Fiber Optics Conference*, pp. 115–119, McLean, Va., U.S.A. (March 1992).)

The use of optical fibers for remote spectroscopy predates the use of fibers in communication systems, and continues to be an important technique in environmental, biomedical and process-control sensing. Recent progress in fiber optic chemical sensing, including the development of optically active sensors, intrinsically sensitive fibers, new sensor chemistries, and sensors based on integrated optic devices, has greatly expanded the range of application of chemical and environmental fiber optic sensors.

Two main configurations can be considered, using either the end fiber or the evanescent wave technique. In the first case, a dye-doped material (polymer or porous glass) is attached to the end of an optical fiber which is only used to relay the sensitive dye fluorescence (or absorption) signal. In the second case, the fiber itself becomes part of the sensing element, which consists of a dye-doped cladding coated onto the fiber core. The evanescent field of a guided radiation can excite the dye, which interacts selectively with the analyte and modulates the light signal. This approach offers a shorter response time and a distributed sensing; a spatial profile of the analyte concentration is provided along the length of the fiber.

Though it may not be apparent in first examination of current work on development of fiber optic sensors for hazardous materials, much of this research involves immobilization of the indicator molecules. Examples of substrates examined recently include porous glass and porous polymers (see, e.g., M. Bocci, F. Baldwin and S. Bracci, "Spectroscopic Behavior of Acid-Base Indicators after Immobilization on Glass Supports," *Appl. Spectrosc.*, Vol. 45, No. 9, pp. 1508–1515 (1991); and M. B. Tabacco, Q. Zhou, K. Rosenblum and M. R. Shahriari, "Chemical Sensors for Hazardous Waste Monitoring," *Proc. of the Second International Symposium on Field-Screening Methods for Hazardous Wastes and Toxic Chemicals*, U.S. Environmental Protection Agency, Las Vegas, Nev., U.S.A. (February 1991)); M. Bocci, F. Baldinin and S. Bracci, "Spectroscopic Behavior of Acid-Base Indicators after Immobilization on Glass Supports," *Appl. Spectrosc.*, Vol. 45, No. 9, pp. 1508–1515 (1991); and C. Rottman, M. Ottolengi, R. Zusman, et al., "Doped Sol-Gel Glasses as pH Sensors," *Matt. Lett.*, Vol. 13, pp. 293–298 (1992)); linear-chain, rigid-rod polymers (W. P. Carey and B. S. Jorgensen, "Optical Sensors for High Acidities Based on Fluorescent Polymers," *Appl. Spectrosc.*, Vol. 45, No. 5, pp. 834–838 (1991)); polybenzimidazol and Formvar$^R$ (L. C. Baylor and P. E. O'Rourke, "Fiber Optic pH Sensors," *NUCL 89, Abstracts of Papers*, 201st American Chemical Society National Meeting, Atlanta, Ga., U.S.A. (April 1991)); cellulose acetate (T. P. Jones, S. J. Coldron, W. J. Deninger and M. D. Porter, "A Field-Deployable Dual Wavelength Fiber Optic pH Sensor Instrument Based on Solid-State Optical and Electrical Components," *App. Spectrosc.*, Vol. 45, No. 8, pp. 1271–1276 (1991)); quartz powder (M. F. McCurley and W. R. Seitz, "Fiber Optic Chemical Sensors Based on Polymer Swelling," *ANYL 61, Abstracts of Papers*, 201st American Chemical Society National Meeting, Atlanta, Ga., U.S.A. (April 1991)); poly(vinyl alcohol) with oxiran group (J. Reichert, R. Czolk, W. Sellien and A. J. Ache, "Chemical Sensors in Environmental Analysis: Ammonium and Cadmium Sensors," *NATO ASSI Ser.*, Ser G 1991, pp. 195–211 (*Chem. Abstr.* 115:84318p)); dimethyl silicone powder (S. M. Barnard and D. R. Walt, "Fiber Optic Organic Vapor Sensor," *Environ. Sci. Techn.*, Vol. 25, No. 7, pp. 1301–1304 (1991)); and cellulose triacetate (C. Jian and W. R. Seitz, "Membrane for In Situ Optical Detection of Organic Nitro Compounds Based on Fluorescence Quenching," *Anal. Chim. Acta*, Vol. 237, No. 2, pp. 265–271 (1991)).

Ethyl cellulose has been proposed as a coating standard for mass sensors, but could be used as a "standard" substrate for fiber optic sensors as well (see, e.g., E. J. Poziomek, J. Li, H. Wohitjen and N. L. Jarvis, "Ethyl Cellulose as a Coating Standard for Mass Sensors," *Third International Symposium on Field Screening Methods for Hazardous Wastes and Toxic Chemicals*, Las Vegas, Nev., U.S.A. (February 1993)).

However, design of immobilized indicator materials, and meeting needs of sensitivity and selectivity are not trivial, as pointed out and explained by E. J. Poziomek, "Technology Barriers in the Development of Fiber Optic and Other Chemical Sensors for Field Screening," *Oak Ridge National Laboratory Life Sciences Symposium*, Gatlinburg, Tenn., U.S.A. (May 1990), published in *Hazardous Waste Site Investigation*, R. B. Gammage and B. A. Berven, Eds., Lewis Publishers, Ann Arbor, Mich., U.S.A. (1992).

Furthermore, there is a severe drawback in incorporating the organic indicator dyes into the traditional host matrices. Depending on the nature of the polymer, the sensor probe is not necessarily inert with respect to the dye, as free radicals tend to be formed under photo-excitation. These radicals tend to strongly reduce the absorption and luminescence characteristics of the dyes. The polymeric matrices may also provide a reductive atmosphere, which will react with the photo-excited states of the dyes and will change their chemical constitution with time. It is therefore of vital interest to develop inert, highly transparent host matrices which are stable and which can be used for remote sensors for environmental and biological impurities.

Purely inorganic matrices, on the other hand, furnish too polar environment for entrapped organic indicator molecules, which may cause them to agglomerate at high concentrations and thus prevent high sensitivity.

In 1990, the present inventor and others published an article, entitled "Oxazine-170 in Sol-Gel Glass and PMMA Films as a Reversible Optical Waveguide Sensor for Ammonia and Acids," (V. Chernyak, R. Reisfeld, R. Gvishi and D. Venezky, *Sensors and Materials,* Vol. 2, No. 2 pp. 117–126 (1990)). In this article, there were described sensors for ammonia and acids based on Oxazine-170 dye, incorporated into sol-gel glasses prepared from tetraethoxysilane. However, the kinetics of the ammonia diffusion was too slow to be used for practical purposes, if the films were not thin enough. On the other hand, Oxazine-170, incorporated into polymethylmethacrylate (PMMA) gave a very good response; however, the sensor was not stable enough and deteriorated quickly.

Earlier in 1993, the present inventor published a further article, entitled "Photochemical SeBased on Malachite Green in Glass Films," (V. Chernyak and R. Reisfeld, *Sensors and Materials,* Vol. 4, No. 4, pp. 195–204 (1993)). As described and explained therein, glass films containing malachite green are sensitive glass waveguide sensors (optrodes) for acid and ammonia vapor or solutions. The different color changes are the result of the yellow $H(MG)^{2+}$ dication, blue-green monocation $(MG)^+$ and colorless carbinol base $HO(MG)$, and depend on the pH of the. surroundings. The method enables the preparation of optically active waveguides with the sensitivity of 1–2 ppm for ammonia. These sensors are all solid state, based on organic indicators incorporated in sol-gel matrices. The concept of applying optical guides and fiber optical sensors for detection of various environmental impurities has been suggested recently (J. Janata and A. Bezegh, *Anal. Chem.,* Vol. 60, p. 62R (1988 and 1990)).

In 1996 present inventors published an article "Reversible Optical Sensor for In Situ Determination of Heavy Metal Impurities in the Environment". (*D. Shamrakov* and R. Reisfeld, *Sensors and Materials,* 8, (1996) 439–443). A technique was suggested for generation of nanoporous sol-gel silica coatings with fluorescent indicator entrapped in it. An optimal structure was achieved, where on one hand the pores were wide enough to provide fast migration of the analyte ions to the indicator molecules inside the glass, but small enough, on the other hand, to prevent the dye leaching and thus sensor deterioration. Reversible operation of sensor for cadmium was demonstrated, which was not however free of disadvantages of an inorganic matrices mentioned above.

In principle, such a system may be composed of a small light source, for example, a light-emitting diode (LED) coupled with a capillary tube covered by a reagent which, by reacting with the impurities, changes its color. The activated tube may be coupled to a filter and photodetector, which appropriately measures either transmission of light or emission induced by the light of the reaction product. In this way it is possible to detect and quantitatively measure traces of ammonia, acids (acid rain) and biological impurities.

While it was found that malachite green was indeed a useful indicator dye in such a system, the sol-gel matrix employed was still unsatisfactory.

SUMMARY OF INVENTION

With the above-described state of the art in mind, according to the present invention there is now provided an indicator dye nanoporous photochemical sensor composite glass film, comprising a multiplicity of polyacrylate chains intertwined with a multiplicity of cross-linked networks of silica and doped with an indicator dye, wherein said film is formed with a plurality of nanopores sized in the range between 20 and 200 angstrom for the entry of analytes to be detected thereby In another aspect of the present invention, there is now provided a process for the preparation of an indicator dye nanoporous photochemical sensor composite glass, comprising a multiplicity of polyacrylate chains intertwined with a multiplicity of cross-linked networks of silica and doped with an indicator dye, said process comprising the steps of:

a) forming a solution of at least one alkoxysilane precursor, water, ethanol and a catalyst to effect the hydrolysis of said precursor;

b) adding a solvent selected from the group consisting of benzene and toluene;

c) effecting azeotropic distillation of the resulting solution to remove water and alcohol;

d) adding glacial acetic acid and distilling off said original solvent while adding an indicator dye, whereby said benzene or toluene are replaced with glacial acetic acid and any water entrained in said dye is removed by said distillation;

e) introducing a polyacrylate of the general formula I:

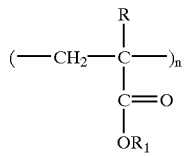

wherein:
R is hydrogen, methyl or ethyl;
$R_1$ is hydrogen, methyl or ethyl, and
n is a whole integer greater than 100
into the remaining solution; and f) distilling off said glacial acetic acid,
whereby there is formed a silica-polymer composite glass solution doped with an indicator dye;

g) applying a coating of said solution on a suitable substrate; and h) evaporation of the solvent under elevated temperature in a closed chamber.

Preferably, in the above formula, n is between 100 and 1,000, R can have different values in the same polymer, and $R_1$ can also have different values in the same polymer.

The invention also provides a wave-guiding sensor comprising a silica-polymer composite glass film doped with an indicator dye, as described herein.

In the above process, it is preferred that the said alkoxysilane precursors have one to four carbon atoms in each of said alkoxy groups; tetraalkoxysilanes, such as tetramethoxysilane, tetraethoxysilane, tetrapropoxysilane and tetrabutoxysilane are preferred.

In an especially preferred embodiment of the present invention, said precursors are tetraalkoxysilane intermixed with a trialkoxysilane derivative having a $C_2$–$C_6$ unsaturated aliphatic chain with one or two double bonds.

Preferred polyacrylates for use in the present invention are polymethylmethacrylate, polyethylmethacrylate, polyacrylic acid and polymethacrylic acid.

In U.S. Pat. No. 5,783,319 by two of the present inventors, there is described and claimed waveguide tunable lasers and processes for the production thereof, wherein a composite glass film waveguide tunable laser is described and claimed. While said lasers are similar to those of the present invention, they are different in structure in that they are continuous and non-porous and therefore cannot be used as photochemical sensors, since analytes cannot enter the film described and formed by the process of said patent. Therefore, said patent neither teaches nor suggests the sensors of the present invention, nor the methods for the production thereof.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF INVENTION

Figure 1:
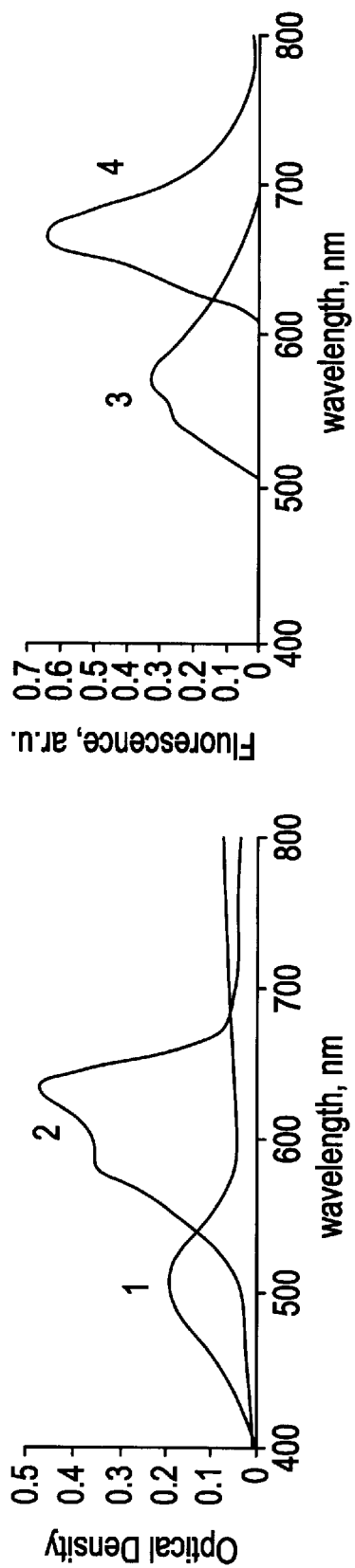
FIG. 1 graphically illustrates the absorption (left) and emission (right) spectra of neutral 1,3 and cationic 2,4 forms of Oxazine-170 in the sol-gel film.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Oxazine-170 as an Indicator

Sol-gel techniques, as described, e.g., in R. Reisfeld and C. K. Jorgensen, Ed., *Chemistry, Spectroscopy and Applications of Sol-Gel Glasses, Structure and Bonding* 77, Springer-Verlag, 265 p. (1992), are utilized in modified form as described hereinbelow for preparation of the silica-polymer composite glass films doped by the indicator dyes. The precursors, tetraethoxysilane (TEOS) $Si(OC_2H_5)_4$ and triethoxyvinylsilane (TEVS) $CH_2=CHSi(OC_2H_5)_3$ were purchased from Fluka and Merck. Polymethylmethacrylate (PMMA) low molecular weight from BDH; glacial acetic acid, benzene and absolute ethanol, from Frutarom.

At the first step, an ordinary sol-gel technique was applied to a homogeneous solution of TEOS, TEVS, water and ethanol in appropriate molar ratio of 0.3:0.7:4:11 in a total volume of 30 ml, and a few drops of glacial acetic acid, hydrochloric acid or sulfuric acid were added as catalyst. After 2 hours of stirring, 25 ml of anhydrous benzene was added. The rest of the water was removed by azeotropic distillation at 65 dC. Then the medium was changed with glacial acetic acid by distillation and solutions of PMMA (1.23 g) and Oxazine-170 dye were added. The excess of the acetic acid was distilled out, to reach the initial volume. As a result, a colloidal solution containing both silica and polymer species was obtained, which remained perfectly stable and clear for a term of up to one month. The derived solid composite material contained 50% by weight of silica.

The films were prepared either by dip-coating or spin-coating on microscope glass slides, inside a dust-free zone. The substrates were soaked overnight in basic solution, then rinsed thoroughly with acid and de-io, zed water before the coating, so as to provide better adherence. The films were dried at 60° C. immediately after coating in closed glass Petri dishes.

Mechanically and photochemically stable films were manufactured, with 0.5–15 $\mu$m thickness, density of about 1.68 g/cm$^3$ and a refractive index of 1.48 at 632 nm.

When ordinary BK-7 glass with a refractive index of 1.51 is used as a substrate material, the flat plate can be used as the planar optical waveguide, while the use of the fused silica (1.46) provides the waveguide properties to the film itself. Similarly, the substrate for the waveguide can be of tubular configuration, with the film being deposited either on the outer or the inner surface of the waveguide tube.

Sensor Response Results

The sensor response can be detected and measured quantitatively, using either the absorption or the emission spectra of the neutral or cationic form of the Oxazine-170 dye.

Figure 2:
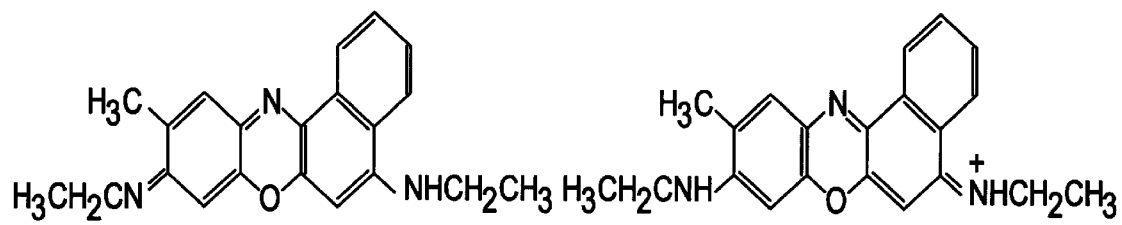
FIG. 2 illustrates the cationic and neutral forms of Oxazine-170.

FIG. 1 presents the absorption spectrum on the left, and the emission (under 400 nm excitation) spectrum on the right, of the neutral (1) and cationic (2) forms of Oxazine-170 in sol-gel films. FIG. 2 demonstrates these cationic and neutral forms.

The acid form is obtained under exposure of the glass films or coated fiberfibers either to acid vapor or to dilute solution of acids. The neutral form is obtained by immersion into the ammonia solution or by exposure to the gaseous ammonia. The color change is completely reversible. The response time, depending on the thickness of the film, varies from 1 sec for 0.5 μm films, to 30 sec for 15 μm films. The detection limits for both ammonia and acids are down to the ppb region.

EXAMPLE 2

Malachite Green as an Indicator

Malachite green (MG), introduced into glass, exhibits a characteristic spectral behavior, depending on the mode of preparation of the glass and its environment. Neutral, monocation and dication forms can be prepared. In acidic glass, the yellow $H(MG)^{2+}$ protonated dications are predominant; the green monocation $MG^+$ exists in water and other media at pH 4 to 6; the colorless carbinol base $HO(MG)$ at higher pH. Uniquely high luminescence yields indicate the formation of chemical bonds between $MG^+$ and the silicate groups, suggesting that the Lewis acid behavior of the three coordinated carbon influences the absorption and luminescence properties of the dye.

Figure 3:
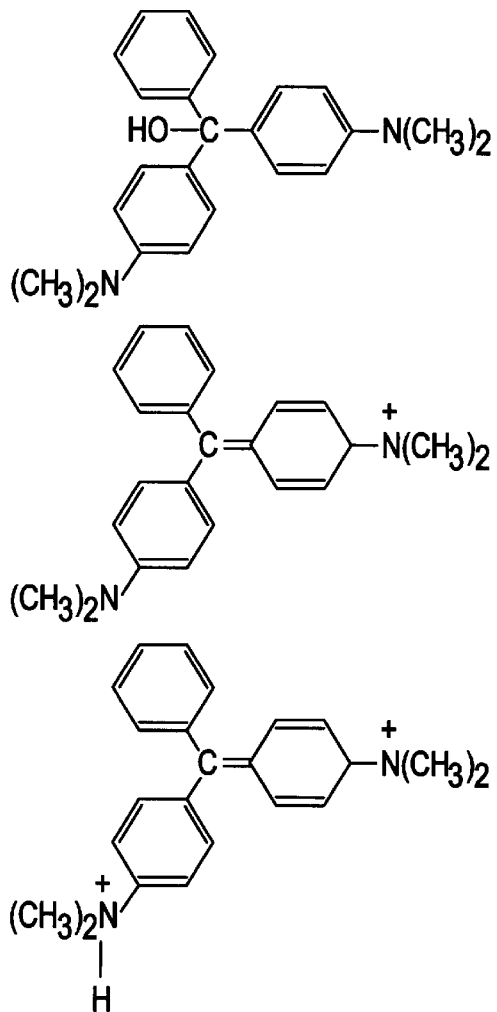
FIG. 3 illustrates the neutral, monocation and dication forms of the malachite green dye downward.

A simplified scheme. of the three main forms of MG is presented in FIG. 3. In glass films, the neutral form has its main absorption peak in the range of 250–300 nm, the monocation form has three main peaks in the ranges 614–629 nm, 420–425 nm and 312–216 nm (three singlet states), and the dication has a peak in the range of 434–460 nm. When the monocation of form of MG is exposed to ammonia vapor, the blue color of the dye becomes colorless (the three peaks in the visible absorption spectrum decrease as a function of pH).

For the purpose of the detection of ammonia, we have utilized the equilibrium between the dication (yellow) the monocation (blue) and the neutral form (colorless).

Preparation of the Films

The composite glass films doped with the malachite green dyes were prepared by the same method as described above in Example 1.

Sensor Response Results

Figure 4:
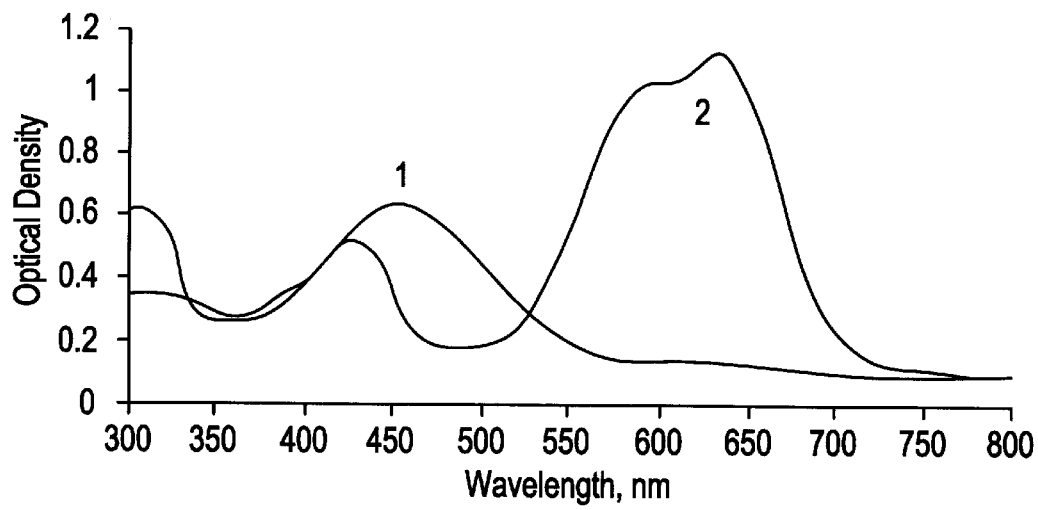
FIG. 4 graphically illustrates the change in the absorption spectrum of malachite green in sol-gel film when exposed to gaseous ammonia.

In FIG. 4, the response of the sensor is shown when the colorless film treated with gaseous ammonia becomes blue.

Figure 5:
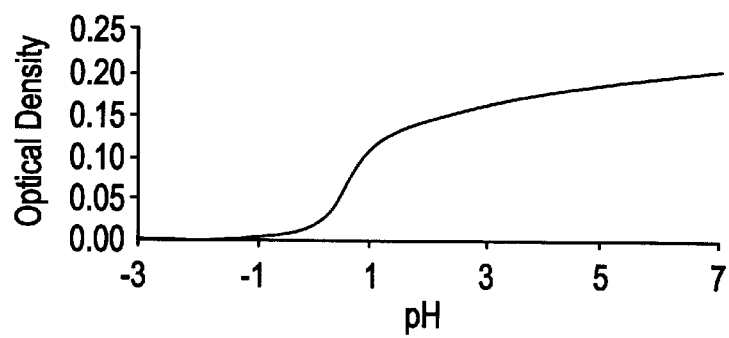
FIG. 5 graphically illustrates the pH sensitivity of a sol-gel film sensor doped with malachite green, immersed entirely in solutions with different pH.

An example of calibration curve is presented in FIG. 5. A film sample was immersed in a series of solutions varying from pH 6.7 to 1 and having Hammet $h_o$ acidity functions 1 to −2. The optical density of the monocation at 622 nm is plotted against pH.

The sensitivity of the sensor to gaseous ammonia and acids is in the ppb region.

EXAMPLE 3

A possibility exists to apply the sensors described in Examples 1 and 2 to distinguish and to measure the ammonium $NH_4+$ ions in a non-acidic media containing other interferingcations. Therein the sensing glass is to be used in optrode configuration, as shown in FIG. 6.

Figure 6:
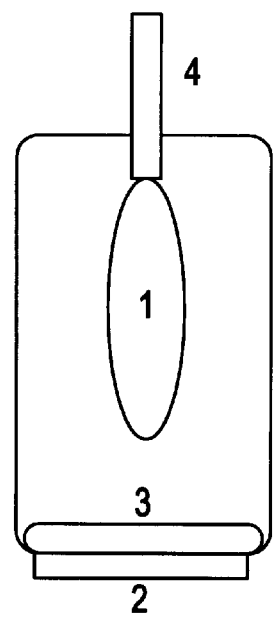
FIG. 6 is a schematic representation of an optrode configuration for ammonium ion measurement.

Referring now to FIG. 6, there is shown the sensing body 1 connected to optical fiber 4 delivering the light. The bottom of the optrode chamber is sealed with a hydrophilic polymer membrane 2 having a layer 3 of solid, finely ground NaOH in mineral oil spread on it as the second liquid membrane. The ammonium ions from the optrode environment react with the base in the boundary between the polymer and liquid membranes giving free ammonia, which penetrates the liquid membrane reaching the space surrounding the sensing body and causes the corresponding response:

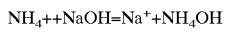

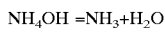

The reaction is performed in neutral or basic medium.

Luminescent Sensors for Chlorinated Hydrocarbons

Fiber optic optrodes were recently proposed (see, e.g., F. P. Milanovich, D. G. Garvis and S. M. Angel, "Remote Detection of Organochlorides with a fiber Optic Based Sensor," *Anal. Inst.*, Vol. 15, p. 137 (1986); and S. M. Angel, M. N. Ridley, et al., "New Developments and Applications of fiber-Optic Sensors," in *Chemical Sensors and Microinstrumentation,* ACD Symposium Series 403, pp. 345–362 (1989)), as based on Fujiwara reaction of base sponsored cleavage of a pyridine ring in the presence of chlorinated hydrocarbons. This reaction leads to formation of highly fluorescent products but is, however, irreversible.

A row of indicator dyes and laser dyes listed in the table below contain nitrogen atoms in their molecules, providing them an opportunity to form weak complexes of Van-der-Waals type with chlorinated hydrocarbons. This complexation causes certain changes in excitation and emission of these dyes, which can be used for their reversible and quantitative assessment.

EXAMPLE 4

Rhodamine 6G Dye as an Indicator

A sensor was prepared in the same manner as described above in Example 1 comprising Rhodamine 6G dye, and its response was measured when a chloroform vapor source was connected to the sensor.

Figure 7:
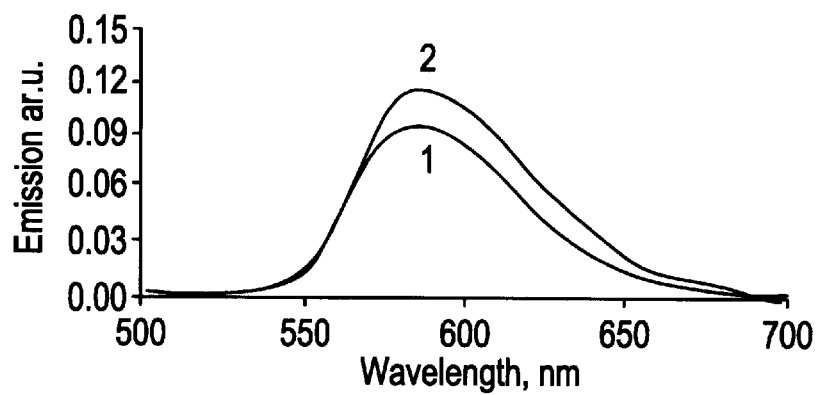
FIG. 7 graphically illustrates the response of the sensor with Rhodamine 6G dye to the presence of chloroform vapor.

The response of the sensor, as graphically shown in FIG. 7, is entirely reversible and the sensitivity reaches the ppb region.

EXAMPLE 5

Oxazine-170 as an Indicator

A sensor was prepared in the same manner as described above in Example 1 comprising Oxazine-170 dye as the indicator, and its response was measured when a dichloroethane vapor source was connected to the sensor.

Figure 8:
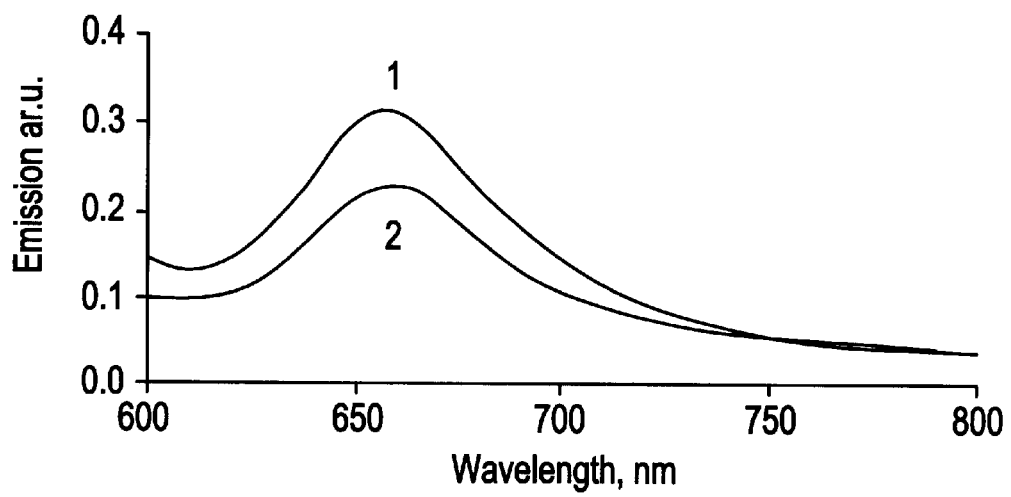
FIG. 8 graphically illustrates the response of the sensor with Oxazine-170 dye to the presence of dichloroethane vapor, and FIG. 9 schematically presents an optic sensor arrangement according to the present invention.

The response of the sensor, as graphically shown in FIG. 8, is entirely reversible and the sensitivity reaches the ppb region.

The Optfiber Sensor Design

Figure 9:
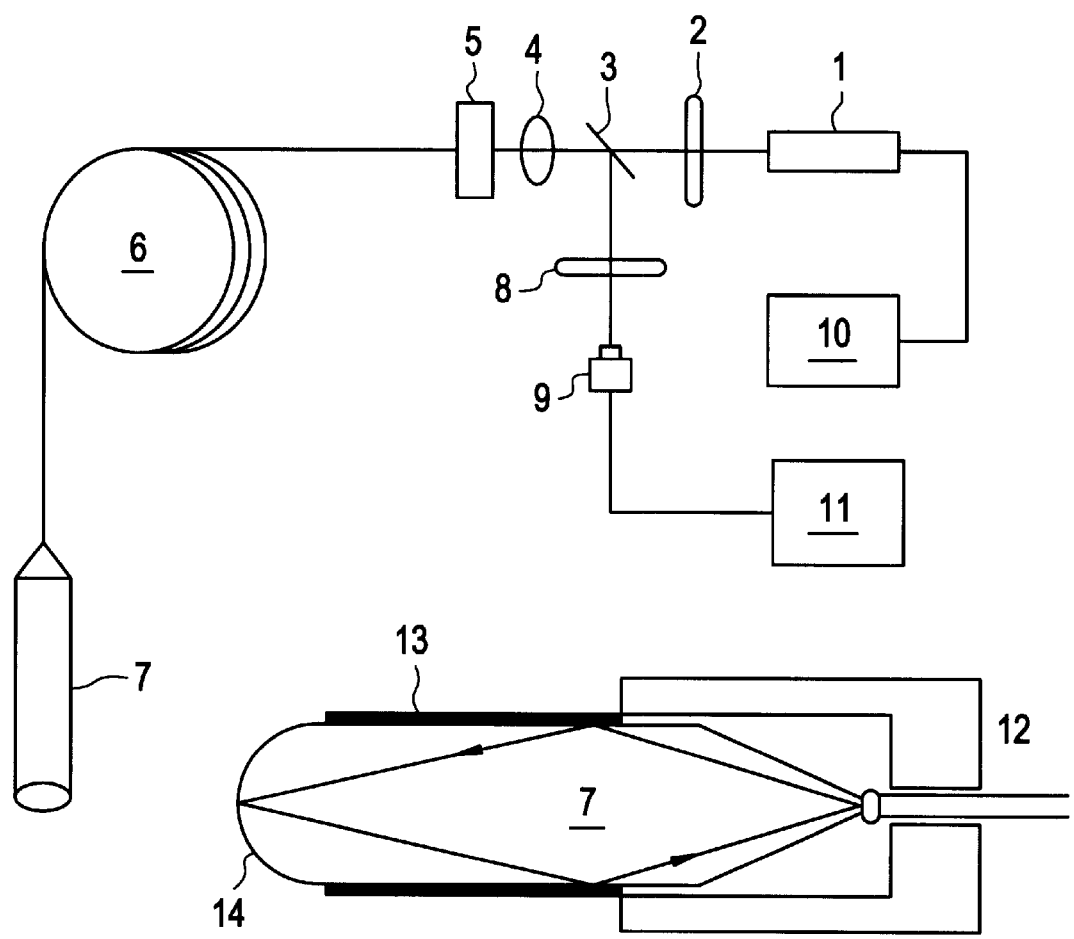

The scheme of optical fiber sensor arrangement is presented in FIG. 9, in which the numerals designating the various components are as follows:

1 light source
2 exciting light filter
3 dichroic mirror
4 lens
5 positioner
6 optical fiber
7 glass sensor body
8 fluorescence light filter
9 photo diode
10 power supply 11 registrator
12 teflon ferrule
13 sensitive film coating
14 silvered spherical face The sensor body 7, which is made of glass (shown in the lower right corner of FIG. 9) is constructed as a 10–20 cm length rod of 4–6 mm diameter, one end thereof being spherical and the other end being conical. The conical end of the rod is polished into a 1 mm diameter circle, for attaching the optical fiber. The optical merger between this circle and the fiber end is made with epoxy glue, and the connection is fixed inside the Teflon ferrule 12. The spherical end 14 of the rod is silvered, providing entire reflection of incident light. The entire cylindrical surface of the rod is uniformly coated with the sensing sol-gel film 13. Multimode, fused silica fiber with a 200 m core is applied for light delivery.

The measurement system operates in two modes, depending upon whether luminescent or absorption indicator dye is applied in the sensing unit. The light source with filter 2, focussing and detection systems are common to both modes. When changing from luminescence to absorption measurement, the filter 8 is not used, and the dichroic mirror 3 is exchanged with a beam splitter.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An indicator dye nanoporous photochemical sensor composite glass film, comprising a multiplicity of polyacrylate chains intertwined with a multiplicity of cross-linked networks of silica and doped with an indicator dye, wherein said film is formed with a plurality of nanopores having a radius sized in the range between 20 and 200 angstroms for the entry of analytes to be detected thereby.

2. An indicator dye nanoporous photochemical sensor composite glass film according to claim 1, wherein said silica networks include $C_2$–$C_6$ carbon chains having at least one double bond.

3. An indicator dye nanoporous photochemical sensor composite glass film according to claim 1, wherein said silica networks include vinyl moieties attached thereto.

4. An indicator dye nanoporous photochemical sensor composite glass film according to claim 1, wherein said silica networks include $C_2$–$C_6$ carbon chains having an epoxy moiety as a part thereof.

5. An indicator dye nanoporous photochemical sensor composite glass film according to claim 1, wherein said silica network is formed from alkoxysilane precursors.

6. An indicator dye nanoporous photochemical sensor composite glass film according to claim 5, wherein said alkoxysilane precursors have 1 to 4 carbon atoms in each of said alkoxy groups.

7. An indicator dye nanoporous photochemical sensor composite glass film according to claim 5, wherein said precursors are tetraalkoxysilanes.

8. An indicator dye nanoporous photochemical sensor composite glass film according to claim 7, wherein said precursors are tetraalkoxysilanes intermixed with a trialkoxysilane derivative having a $C_2$–$C_6$ unsaturated aliphatic chain with one or two double bonds.

9. An indicator dye nanoporous photochemical sensor composite glass film according to claim 7, wherein said precursors are tetraalkoxysilanes intermixed with a trialkoxysilane derivative having a $C_2$–$C_6$ unsaturated aliphatic chain having an epoxy moiety as a part thereof.

10. An indicator dye nanoporous photochemical sensor composite glass film according to claim 1, wherein said polyacrylate chains are formed from polyacrylates of the general formula I:

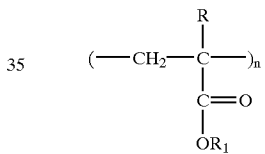

wherein:

R is hydrogen, methyl or ethyl;

$R_1$ is hydrogen, methyl or ethyl, and n is a whole integer greater than 100.

* * * * *